(12) United States Patent
Cao et al.

(10) Patent No.: US 11,854,205 B2
(45) Date of Patent: Dec. 26, 2023

(54) MEDICAL IMAGE SEGMENTATION METHOD AND APPARATUS, COMPUTER DEVICE, AND STORAGE MEDIUM

(71) Applicant: Tencent Technology (Shenzhen) Company Limited, Shenzhen (CN)

(72) Inventors: Shilei Cao, Shenzhen (CN); Kai Ma, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 370 days.

(21) Appl. No.: 17/229,707

(22) Filed: Apr. 13, 2021

(65) Prior Publication Data
US 2021/0233247 A1 Jul. 29, 2021

Related U.S. Application Data

(63) Continuation of application No. PCT/CN2020/074631, filed on Feb. 10, 2020.

(30) Foreign Application Priority Data

Feb. 20, 2019 (CN) .......................... 201910126219.9

(51) Int. Cl.
*G06K 9/00* (2022.01)
*G06T 7/11* (2017.01)
(Continued)

(52) U.S. Cl.
CPC ............... *G06T 7/11* (2017.01); *G06N 3/045* (2023.01); *G06N 3/08* (2013.01); *G16H 30/40* (2018.01);
(Continued)

(58) Field of Classification Search
CPC ............ G06T 7/11; G06T 2207/20081; G06T 2207/20084; G06T 2207/30004;
(Continued)

(56) References Cited

U.S. PATENT DOCUMENTS 10,885,400 B2* 1/2021 Zhao .................. G06N 3/08

FOREIGN PATENT DOCUMENTS

CN 103226708 A 7/2013
CN 105654102 A 6/2016
(Continued)

OTHER PUBLICATIONS

Tencent Technology, WO, PCT/CN2020/074631, May 9, 2020, 5 pgs.
(Continued)

*Primary Examiner* — Xin Jia
(74) *Attorney, Agent, or Firm* — Morgan, Lewis & Bockius LLP (57) ABSTRACT

This application relates to a medical image segmentation method, a computer device, and a storage medium. The method includes: obtaining medical image data; obtaining a target object and weakly supervised annotation information of the target object in the medical image data; determining a pseudo segmentation mask for the target object in the medical image data according to the weakly supervised annotation information; and performing mapping on the medical image data by using a preset mapping model based on the pseudo segmentation mask, to obtain a target segmentation result for the target object. Because the medical image data is segmented based on the weakly supervised annotation information, there is no need to annotate information by using much labor during training of the preset mapping model, thereby saving labor costs. The preset mapping model is a model used for mapping the medical image data based on the pseudo segmentation mask.

20 Claims, 4 Drawing Sheets

(51) Int. Cl.
*G16H 30/40* (2018.01)
*G06N 3/08* (2023.01)
*G06N 3/045* (2023.01)

(52) U.S. Cl.
CPC ............... *G06T 2207/20081* (2013.01); *G06T 2207/20084* (2013.01); *G06T 2207/30004* (2013.01)

(58) Field of Classification Search
CPC .......... G06T 2207/20104; G06N 3/045; G06N 3/08; G16H 30/40; G16H 50/20; G16H 50/70
See application file for complete search history.

(56) References Cited

FOREIGN PATENT DOCUMENTS

| | | | |
|---|---|---|---|
| CN | 105719275 A | 6/2016 | |
| CN | 106228120 A | 12/2016 | |
| CN | 106408562 A | 2/2017 | |
| CN | 106530305 A | 3/2017 | |
| CN | 106997594 A | 8/2017 | |
| CN | 108682015 A | 10/2018 | |
| CN | 108764281 A | 11/2018 | |
| CN | 108898618 A | 11/2018 | |
| CN | 108898618 A | * 11/2018 | ............... G06T 7/11 |
| CN | 108984629 A | 12/2018 | |
| CN | 109033944 A | 12/2018 | |
| CN | 109255790 A | 1/2019 | |
| CN | 109344833 A | 2/2019 | |
| CN | 109872333 A | 6/2019 | |
| WO | WO 2018085749 A1 | 5/2018 | |

OTHER PUBLICATIONS

Tencent Technology, IPRP, PCT/CN2020/074631, Aug. 10, 2021, 6 pgs.
Di Lin, et al. "ScribbleSup: Scribble-Supervised Convolutional Networks for Semantic Segmentation", 2016 IEEE Conference on Computer Vision and Pattern Recognition, Dec. 31, 2016, 9 pgs.
Tencent Technology, ISR, PCT/CN2020/074631, May 9, 2020, 2 pgs.

* cited by examiner

FIG. 8

MEDICAL IMAGE SEGMENTATION METHOD AND APPARATUS, COMPUTER DEVICE, AND STORAGE MEDIUM

CROSS-REFERENCE TO RELATED APPLICATIONS

This application is a continuation application of PCT Patent Application No. PCT/CN2020/074631, entitled "MEDICAL IMAGE SEGMENTATION METHOD AND APPARATUS, COMPUTER DEVICE, AND STORAGE MEDIUM" filed on Feb. 10, 2020, which claims priority to Chinese Patent Application No. 201910126219.9, entitled "MEDICAL IMAGE SEGMENTATION METHOD AND APPARATUS, COMPUTER DEVICE, AND STORAGE MEDIUM", filed on Feb. 20, 2019, all of which are incorporated herein by reference in their entirety.

FIELD OF THE TECHNOLOGY

This application relates to the field of medical image processing, and in particular, to a medical image segmentation method and apparatus, a computer device, and a storage medium.

BACKGROUND OF THE DISCLOSURE

A medical image refers to an image of internal tissue of a human body or a part of the human body obtained in a non-invasive manner for medical treatment or medical research. Medical image segmentation plays an important role in clinical diagnosis decision-making, treatment planning, and intraoperative navigation.

In a medical image segmentation method in the related technology, a pixel/voxel-level annotation needs to be used when a mapping model is trained, which is time-consuming and labor-consuming and requires strong support of doctors, and it is very difficult to obtain a large number of high-quality annotations. Therefore, labor costs of the foregoing medical image segmentation need to be further reduced.

SUMMARY

Based on this, this application provides a medical image segmentation method and apparatus, a computer device, and a storage medium, which can reduce labor costs.

A medical image segmentation method is provided, applicable to a computer device, the method including:
  obtaining medical image data;
  obtaining a target object and weakly supervised annotation information of the target object in the medical image data;
  determining a pseudo segmentation mask for the target object in the medical image data according to the weakly supervised annotation information; and
  performing mapping on the medical image data by using a preset mapping model based on the pseudo segmentation mask, to obtain a target segmentation result for the target object.

A medical image segmentation apparatus is provided, including:
  an image data obtaining module, configured to obtain medical image data;
  an object annotation obtaining module, configured to obtain a target object and weakly supervised annotation information of the target object in the medical image data;
  an initial mask segmentation module, configured to determine a pseudo segmentation mask for the target object in the medical image data according to the weakly supervised annotation information; and
  a target result segmentation module, configured to perform mapping on the medical image data by using a preset mapping model based on the pseudo segmentation mask, to obtain a target segmentation result for the target object.

A computer device is provided, including a memory and a processor, the memory storing a computer program, the processor, when executing the computer program, implementing the following operations:
  obtaining medical image data;
  obtaining a target object and weakly supervised annotation information of the target object in the medical image data;
  determining a pseudo segmentation mask for the target object in the medical image data according to the weakly supervised annotation information; and
  performing mapping on the medical image data by using a preset mapping model based on the pseudo segmentation mask, to obtain a target segmentation result for the target object.

A non-transitory computer-readable storage medium is provided, storing a computer program, the computer program, when executed by a processor, implementing the following operations:
  obtaining medical image data;
  obtaining a target object and weakly supervised annotation information of the target object in the medical image data;
  determining a pseudo segmentation mask for the target object in the medical image data according to the weakly supervised annotation information; and
  performing mapping on the medical image data by using a preset mapping model based on the pseudo segmentation mask, to obtain a target segmentation result for the target object.

In the foregoing medical image segmentation method and apparatus, the computer device, and the storage medium. The method includes: obtaining medical image data; obtaining a target object and weakly supervised annotation information of the target object in the medical image data; determining a pseudo segmentation mask for the target object in the medical image data according to the weakly supervised annotation information; and performing mapping based on the pseudo segmentation mask, the medical image data and a preset mapping model, to obtain a target segmentation result for the target object. Because the medical image data is segmented based on the weakly supervised annotation information, there is no need to annotate information by using much labor during training of the preset mapping model used when mapping is performed based on the pseudo segmentation mask and the medical image data, thereby saving labor costs.

DESCRIPTION OF EMBODIMENTS

To make the objectives, technical solutions, and advantages of this application clearer and more understandable, this application is further described in detail below with reference to the accompanying drawings and the embodiments. It is to be understood that the specific embodiments described herein are only used for explaining this application, and are not used for limiting this application.

Figure 1:
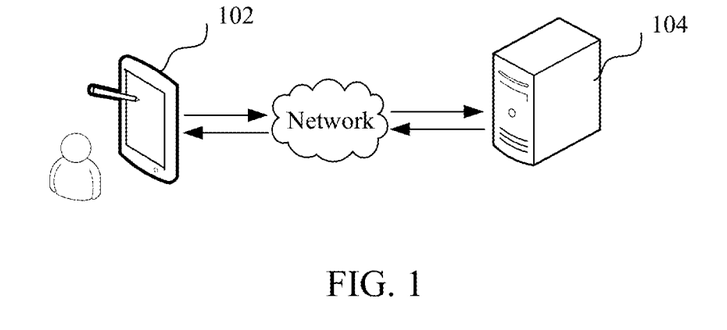
FIG. 1 is a schematic diagram of an application environment diagram of a medical image segmentation method in an embodiment.

FIG. 1 is a schematic diagram of an application environment of a medical image segmentation method in an embodiment. A medical image segmentation method provided in this application is applicable to an application environment shown in FIG. 1. A terminal 102 communicates with a server 104 through a network. The medical image segmentation method in this embodiment of this application may run on the server 104. The terminal 102 may transmit medical image data, a target object and weakly supervised annotation information to the server 104 through a network. The server 104 obtains the medical image data; obtains the target object and the weakly supervised annotation information of the target object in the medical image data; determines a pseudo segmentation mask for the target object in the medical image data according to the weakly supervised annotation information; and performs mapping based on the pseudo segmentation mask, the medical image data and a preset mapping model, to obtain a target segmentation result for the target object. The server 104 may further return the target segmentation result to the terminal. The terminal 102 may be a desktop device or a mobile terminal, for example, a desktop computer, a tablet computer, or a smartphone, or may be a computer device for medical treatment. The server 104 may be an independent physical server, a physical server cluster, or a virtual server.

In an exemplary embodiment, the foregoing medical image segmentation method may be alternatively independently performed by the terminal 102. For the computer device configured to perform the foregoing medical image segmentation method, a specific form is not limited in this application, and may be alternatively another computing form such as cloud computing, or blockchain computing.

Figure 2:
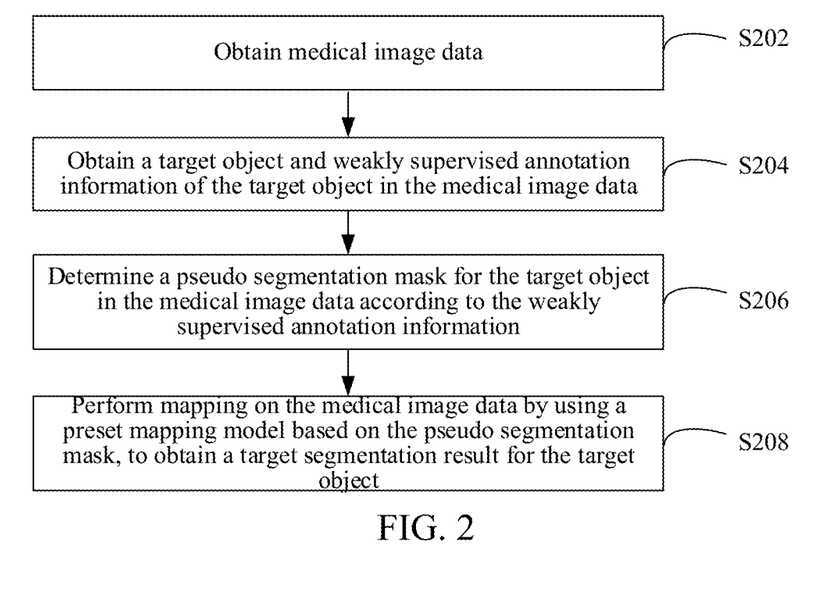
FIG. 2 is a schematic flowchart of a medical image segmentation method in an embodiment.

As shown in FIG. 2, in an embodiment, a medical image segmentation method is provided. This method may be run on the server 104 (or the terminal 102) in FIG. 1. The medical image segmentation method includes the following steps:

S202. Obtain medical image data.

The medical image data may include at least one of two-dimensional medical image data and three-dimensional medical image data. The medical image data may be medical image picture data, or may be medical image video data.

The manner of obtaining the medical image data may be receiving medical image data transmitted by the terminal through a network interface of the server. For example, the medical image data may be medical image data that is transmitted by the terminal requesting a medical image data segmentation service on the server through a preset link, and is transmitted to the server through the network interface. That is, the terminal transmits the medical image data segmentation request.

The manner of obtaining the medical image data may be alternatively that: the server accesses a preset storage position and reads medical image data from the preset storage position. For example, the medical image data may be pre-stored at the preset storage position of the server. When the medical image segmentation is performed, the server reads the medical image data at the preset storage position, so as to obtain the medical image data. The preset storage position is a preset storage position, for example, an uploading position of the terminal or a database storage position of the server, used for storing the medical image data.

The manner of obtaining the medical image data may be alternatively acquiring medical image data, or may be reading acquired medical image data.

S204. Obtain a target object and weakly supervised annotation information of the target object in the medical image data.

The terminal obtains the target object and the weakly supervised annotation information of the target object in the medical image data, and then transmits the target object and the weakly supervised annotation information of the target object in the medical image data to the server through the network interface. The server receives the target object and the weakly supervised annotation information of the target object in the medical image data.

The target object is an object that is expected to be segmented from the medical image data, and may be an image of at least one visceral tissue of a liver, a heart, a lung, a spleen, and a stomach. The weakly supervised annotation information is information used for annotating a position of the target object in the medical image data. Optionally, the weakly supervised annotation information is information used for annotating the position of the target object in the medical image data in simple annotation manners. The simple annotation manners include at least one of performing annotation using points of manual annotation, performing annotation using apostrophes of manual annotation, and performing annotation using bounding boxes of manual annotation.

Different from annotation using a pixel/voxel level, the position information of the target object needs to be annotated in detail at the pixel/voxel level. The weakly supervised annotation does not need to be accurate to the pixel/voxel level, provided that the position information of the target object is roughly annotated manually. The weakly supervised annotation information is information roughly annotating a position of the target object. The position information of the target object may be roughly annotated in a manner of a weakly supervised annotation such as a point, an apostrophe or a bounding box. For example, that the target object is at the position annotated by this point can be represented in a point annotation manner. In another example, that the target object is at the position annotated by this apostrophe is represented in an apostrophe annotation manner. In still another example, that the target object is within a range annotated by this bounding box is represented in a bounding box annotation manner. The point annotation means that the target object is identified by drawing a point on an image. The apostrophe annotation means that the target object is identified by drawing an apostrophe on an image. The bounding box refers to the smallest matrix box that includes a segmented object. The bounding box annotation means that the target object is identified by drawing a bounding box on an image. In the weakly supervised annotation manners, a lot of manual annotation costs can be saved, and compared with an unsupervised annotation manner, a more accurate segmentation result can be also obtained.

The manner of obtaining, by the server, the target object may be that: the terminal receives a target object inputted by the user, the terminal transmits the target object to the server, and the server receives the target object. The manner of user input may be that: a selection interface is provided on the terminal, and the user then inputs in a selection manner. That is, the terminal may receive, in a manner of receiving a selection instruction, the target object inputted by the user, and then forward the received selection instruction to the server, so that the server receives the selection instruction, and analyzes the selection instruction to obtain the target object inputted by the user. The manner of user input may be alternatively that: an interface for inputting the target object is provided on the terminal, and the target object is then inputted in an input manner. That is, the terminal may receive, in a manner of receiving the input instruction, the target object inputted by the user, and then forward the input instruction to the server, so that the server receives the input instruction, and analyzes the input instruction to obtain the target object inputted by the user.

The manner of obtaining, by the server, the target object may be alternatively: obtaining a preset target object. The target object may be preset. When the medical image data needs to be segmented, the preset target object is obtained, to determine that image segmentation is performed on which object in the medical image data.

The manner of obtaining, by the server, the weakly supervised annotation information of the target object in the medical image data may be that: the terminal displays the medical image data, and then receives information annotated by the user on the medical image data. Then, the terminal transmits the weakly supervised annotation information to the server, and the server receives the weakly supervised annotation information in the medical image data.

The manner of obtaining, by the server, the weakly supervised annotation information of the target object in the medical image data may be alternatively: reading content at the preset storage position. For example, a worker may do annotation work on the medical image data in advance, and store the weakly supervised annotation information at the preset storage position. The server obtains the weakly supervised annotation information of the target object in the medical image data in a manner of reading the content at the preset storage position.

S206. Determine a pseudo segmentation mask for the target object in the medical image data according to the weakly supervised annotation information.

The pseudo segmentation mask refers to a segmentation mask that is not manually annotated. The segmentation mask may perform extraction of a region of interest on the medical image data, and perform further image segmentation within the region of interest. The server may obtain an image value of the region of interest by multiplying the pseudo segmentation mask by the medical image data, where the image value within the region of interest remains unchanged, and image values outside the region of interest are all 0. That is, the image values outside the region of interest are shield.

The server may determine a pseudo segmentation mask for the target object in the medical image data according to a type of the weakly supervised annotation information. The type of the weakly supervised annotation information includes at least one of point annotation, apostrophe annotation, and bounding box annotation. When the type of the weakly supervised annotation information is the point annotation or the apostrophe annotation, expansion outward may be performed according to the weakly supervised annotation information according to a preset rule, to obtain the pseudo segmentation mask. When the type of the weakly supervised annotation information is the bounding box annotation, the bounding box region may be used as the pseudo segmentation mask according to the weakly supervised annotation information.

The manner of determining, by the server, a pseudo segmentation mask for the target object in the medical image data according to the weakly supervised annotation information may be alternatively determined by using a trained neural network model. For example, the neural network model may map the weakly supervised annotation information and the medical image data, to obtain the pseudo segmentation mask. In another example, the neural network model may alternatively use the weakly supervised annotation information as a constraint condition, and map the medical image data, to obtain the pseudo segmentation mask. In still another example, the medical image data may be mapped by using an unsupervised learning Grabcut (image segmentation) model, a modified conjugate gradient (MCG) model, or the like, to implement image segmentation, so as to obtain an initial pseudo segmentation mask, and the initial pseudo segmentation mask and the weakly supervised annotation are then combined, to determine the pseudo segmentation mask for the target object in the medical image data.

S208. Perform mapping on the medical image data by using a preset mapping model based on the pseudo segmentation mask, to obtain a target segmentation result for the target object.

The preset mapping model is a neural network model that is pre-trained and performs image segmentation on the target object. That mapping is performed based on the pseudo segmentation mask and the medical image data may be mapping the pseudo segmentation mask and the medical image data, to obtain the target segmentation result for the target object.

That mapping is performed based on the pseudo segmentation mask and the medical image data may be alternatively mapping a corresponding region of interest of the pseudo segmentation mask in the medical image data, to obtain a prediction result for the target object.

The region of interest is a region that is determined by using the pseudo segmentation mask and the medical image data and is of the target object in the medical image data. The region of interest may be determined by multiplying the pseudo segmentation mask by the medical image data. That mapping is performed based on the pseudo segmentation mask and the medical image data may be alternatively mapping the medical image data by using the preset mapping model obtained based on the pseudo segmentation mask, to obtain the target segmentation result for the target object.

In this embodiment, mapping is performed on the medical image data and a preset mapping model based on the pseudo segmentation mask, to implement image segmentation. In this way, the target object in the region of interest corresponding to the pseudo segmentation mask in the medical image data is segmented, so that the image of the target object is distinguished from the region of interest corresponding to the pseudo segmentation mask in the medical image data. Therefore, the target object in the medical image data is segmented, so that the image of the target object is distinguished from the whole medical image data. When the pseudo segmentation mask and the medical image data are mapped to implement image segmentation, the target object in the region of interest may be segmented based on a priori knowledge such as domain knowledge. The a priori knowledge may be knowledge that may be used by machine learning and is for the target object. The domain knowledge is knowledge that is in the field, may be used by machine learning, and is for the target object.

In the foregoing medical image segmentation method, medical image data is obtained; a target object and weakly supervised annotation information of the target object in the medical image data are obtained; a pseudo segmentation mask for the target object in the medical image data is determined according to the weakly supervised annotation information; and mapping is performed on the medical image data and a preset mapping model based on the pseudo segmentation mask, to obtain a target segmentation result for the target object. Because the medical image data is segmented based on the weakly supervised annotation information, there is no need to annotate information by using much labor during training of the preset mapping model used when mapping is performed on the medical image data based on the pseudo segmentation mask, thereby saving labor costs.

Further, compared with the embodiments of this application, in the medical image segmentation method based on the pixel/voxel-level annotation, at least more than 15 times of doctor annotation time in this embodiment of this application is consumed. That is, in the medical image segmentation method provided in this application, more than 14 times of labor costs can be saved. A doctor who performs pixel/voxel-level annotation on the medical image data needs to be a doctor who is highly experienced in pathological diagnosis associated with the target object, for example, a doctor with over 10 years' experience.

In an embodiment, the mapping on the medical image data and a preset mapping model based on the pseudo segmentation mask, to obtain a target segmentation result for the target object includes: performing mapping on the medical image data based on the pseudo segmentation mask by using at least two preset mapping models, to obtain at least two intermediate segmentation results for the target object; and fusing the at least two intermediate segmentation results, to obtain the target segmentation result for the target object.

The manner of performing mapping the medical image data based on the pseudo segmentation mask by using at least two preset mapping models may be separately mapping by using each preset mapping model based on the pseudo segmentation mask and the medical image data by using the at least two preset mapping models, to obtain at least two intermediate segmentation results for the target object.

The manner of fusing the at least two intermediate segmentation results may be fusing the at least two intermediate segmentation results in a preset fusion manner. In an example, the server may perform a weighted summation on the at least two intermediate segmentation results, so as to fuse the at least two intermediate segmentation results. To further improve the accuracy of the medical image segmentation method, intermediate segmentation results that meet a preset condition in the at least two intermediate segmentation results may be further fused, so as to fuse the at least two intermediate segmentation results.

The preset condition is a preset filtering condition. For example, the preset condition may be that results with obvious errors in the intermediate segmentation results are filtered, and do not participate in fusion. In another example, the preset condition may be that intermediate segmentation results whose confidence levels are lower than a preset value are filtered, and do not participate in fusion.

Based on the medical image segmentation method in this embodiment, when mapping is performed on the medical image data and a preset mapping model based on the pseudo segmentation mask, to obtain a target segmentation result for the target object, mapping is performed by using the at least two preset mapping models, so that mapping may be performed on the medical image data based on the pseudo segmentation mask to obtain at least two intermediate segmentation results. The at least two intermediate segmentation results are then fused to obtain a prediction result for the target object, thereby improving the accuracy of the target segmentation results.

Figure 3:
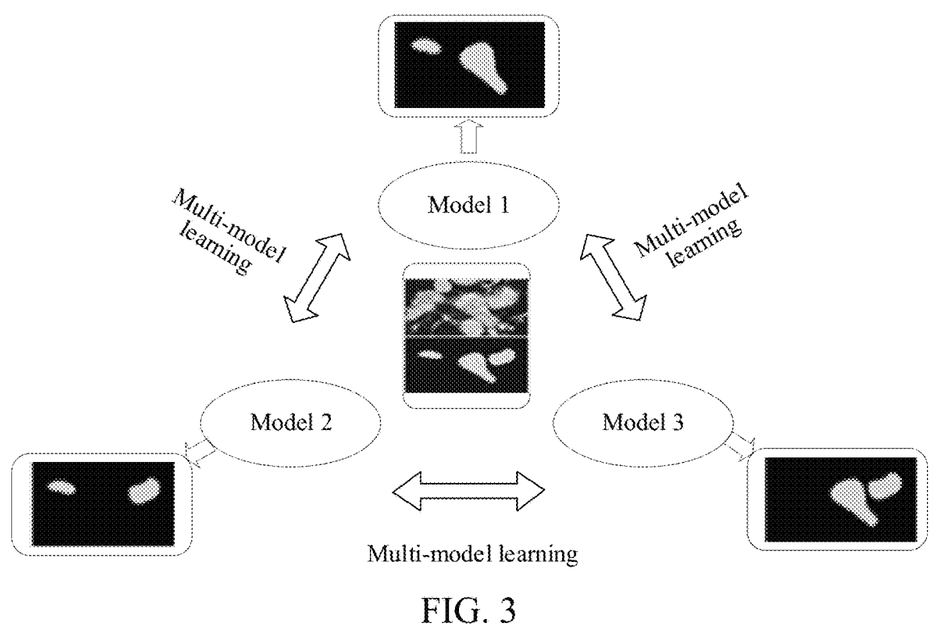
FIG. 3 is a schematic principle diagram of a medical image segmentation method in an exemplary embodiment.

In an example, left atrium segmentation is used as an example. As shown in FIG. 3, a left atrium shown in FIG. 3 includes three connected regions. If prediction of a single model is relied on, only two connected regions (as shown in three vertices in FIG. 3, the three vertices are connected regions predicted by a model 1, a model 2, and a model 3 respectively) can be predicted. In a case of multi-model fusion, after fusing the connected regions predicted by the model 1, the model 2, and the model 3 respectively, the server may predict a complete structure (as shown in a middle region in FIG. 3) of the left atrium.

In an example, the mapping on the medical image data based on the pseudo segmentation mask by using at least two preset mapping models, to obtain at least two intermediate segmentation results for the target object includes: performing mapping on the medical image data based on the pseudo segmentation mask by using at least two neural network models with no less than two structural types, to obtain the at least two intermediate segmentation results for the target object. That is, the at least two preset mapping network models are at least two neural network models, and a quantity of structural types of the neural network models is not less than 2. In an exemplary embodiment, a quantity of structural types of the neural network models is the same as a quantity of neural network models. That is, structural types of each neural network model are different. The structural type of the neural network model may be any deep network model with a segmentation capability.

Mapping is performed based on the pseudo segmentation mask and the medical image data by using the neural network model with at least two structures, to obtain at least two intermediate segmentation results for the target object. In this way, mapping may be performed, based on the pseudo segmentation mask, on the medical image data by using the neural network model with different structures, to obtain at least two intermediate segmentation results for the target object. Therefore, the accuracy of the target segmentation results for the target object obtained by fusing the at least two intermediate segmentation results can be further improved, thereby improving the accuracy of the medical image segmentation.

In an embodiment, in a training process of the at least two preset mapping models, the server trains the at least two preset mapping models in a self-paced learning manner.

The self-paced learning manner is a manner that, in the training process, results obtained through a previous round of training after being screened are used as an input of a next round of training. The process of screening the samples in the self-paced learning process may be regarded as a weighting method for the samples. The self-paced learning manner may automatically complete a learning process from easy to difficult by using the model. The training the at least two preset mapping models in a self-paced learning manner can improve the stability of iteratively inputting the data in the training process. In this way, the stability of the preset mapping models obtained through training can be improved, so that the stability of the medical image segmentation can be improved based on the medical image segmentation method in this embodiment.

In an embodiment, the training process of the at least two preset mapping models includes: training at least two intermediate preset mapping models based on the pseudo segmentation mask in the training process; performing mapping based on the medical image data in the training process by using the at least two intermediate preset mapping models, to obtain at least two predicted training segmentation results; generating an advanced pseudo segmentation mask according to the predicted training segmentation results that meet a confidence condition in combination with a priori knowledge; and retraining the at least two intermediate preset mapping models based on the advanced pseudo segmentation mask until a preset stop condition is met, to obtain the preset mapping models.

The server may use the pseudo segmentation mask obtained in the training process as the input of the model, to train the at least two intermediate preset mapping models; or may use both the pseudo segmentation mask and the medical image data obtained in the training process as inputs of the preset mapping models, to train the at least two intermediate preset mapping models; or may use the pseudo segmentation mask as a label of the medical image data in the training process, and perform training based on the label, that is, the pseudo segmentation mask, and a loss function of the target segmentation results, to obtain at least two intermediate preset mapping models. The is a loss function of the target segmentation results in training.

The confidence condition may be that the confidence level is higher than the preset value. The confidence refers to a probability value in the results obtained by using the model. The probability value represents a probability that the target segmentation result is consistent with a real result in the mapping process. The term "model" in this specification is a general term of the preset mapping model and the intermediate preset mapping model.

The present stop condition may be that a maximum quantity of times of iterations is reached. The maximum quantity of times of iterations may be a value of a quantity of times of iterations set by a technical personnel, or may be a quantity of times corresponding to an iteration time set by a technical personnel. When the preset stop condition is met, a last intermediate preset prediction model is used as the preset mapping model.

Based on the medical image segmentation method in this embodiment, the predicted training segmentation results are screened based on the confidence of the prediction result to obtain an advanced pseudo segmentation mask, so as to screen the training samples, and a next round of model training is performed until the preset stop condition is met, to obtain the preset mapping models. In this way, the selection of confidences of the samples is enhanced, so that the training of the preset mapping models is more stable, thereby improving the stability of the medical image segmentation.

In an embodiment, the mapping on the medical image data and a preset mapping model based on the pseudo segmentation mask, to obtain a target segmentation result for the target object includes: mapping the medical image data by using the preset mapping model obtained based on the pseudo segmentation mask, to obtain the target segmentation result for the target object.

The preset mapping models obtained based on the pseudo segmentation mask may use the pseudo segmentation mask as an annotation of the medical image data in the training process, and perform training based on the annotation, that is, the pseudo segmentation mask, and the loss function of the target segmentation results in training, to finally obtain the preset mapping models. The medical image data is then mapped by using the preset mapping model obtained based on the pseudo segmentation mask, to obtain the target segmentation result for the target object. That is, the medical image data is inputted to the preset mapping model, to obtain an output result of the preset mapping model, that is, the target segmentation result for the target object.

Based on the medical image segmentation method in this embodiment, in the process of obtaining the preset mapping models, a large amount of pixel/voxel-level manual annotation work does not need to be performed on the medical image data. Therefore, a lot of labor costs can be saved.

In an embodiment, the mapping of the medical image data based on the pseudo segmentation mask, to obtain the target segmentation result for the target object includes: performing mapping based on the pseudo segmentation mask and the medical image data, to obtain a predicted segmentation result for the target object; and correcting the predicted segmentation result according to the a priori knowledge and/or the weakly supervised annotation information, to obtain the target segmentation result.

The correction on the predicted segmentation result is a further improvement on the prediction analysis result according to the a priori knowledge and/or the weakly supervised annotation information, to correct obvious errors that possibly exist in the predicted segmentation result, or to further improve the accuracy of the predicted segmentation result.

The correction on the predicted segmentation result according to the a priori knowledge may enable that the obtained target segmentation result conforms to the a priori knowledge. In this way, the obvious errors can be avoided, thereby further improving the accuracy of the target segmentation result.

The correction on the prediction analysis result according to the weakly supervised annotation information may enable that the obtained target segmentation result is constrained by the weakly supervised annotation information. In this way, the obvious errors can be also avoided, thereby further improving the accuracy of the target segmentation result.

The correction on the predicted segmentation result according to the a priori knowledge and the weakly supervised annotation information may enable that the obtained target segmentation result is constrained by both the a priori knowledge and the supervised annotation information. In this way, the obvious errors can be better avoided, and the accuracy of the target segmentation result is better improved, thereby improving the accuracy of the medical image segmentation.

In an embodiment, the determining a pseudo segmentation mask for the target object in the medical image data according to the weakly supervised annotation information includes: determining the pseudo segmentation mask for the target object in the medical image data based on the a priori knowledge and the weakly supervised annotation information.

The a priori knowledge may be knowledge that may be used by machine learning and is related to the target object. The a priori knowledge may include a priori knowledge of a target object contour, a a priori knowledge of a target object structure, and the like. The a priori knowledge of the target object may include a priori knowledge of the medical image data when the medical image data is segmented, and a priori knowledge of the segmentation result obtained when the medical image is segmented. Strong a priori knowledge exists during the medical image segmentation. For example, a Hounsfield unit of CT has physical meaning, and organic tissue structures of each person are similar.

The manner of determining the pseudo segmentation mask for the target object in the medical image data based on the a priori knowledge and the weakly supervised annotation information may be determining a pseudo segmentation mask for the target object in the medical image data according to the weakly supervised annotation information and a type of the weakly supervised annotation information. The type of the weakly supervised annotation information may include point annotation, apostrophe annotation, and bounding box annotation. When the type of the weakly supervised annotation information is the point annotation or the apostrophe annotation, expansion outward may be performed according to the weakly supervised annotation information according to a preset rule, to obtain the pseudo segmentation mask. When the type of the weakly supervised annotation information is the bounding box annotation, the bounding box region may be used as the pseudo segmentation mask according to the weakly supervised annotation information.

The manner of determining the pseudo segmentation mask for the target object in the medical image data based on the a priori knowledge and the weakly supervised annotation information may be alternatively determined by using a trained neural network model. For example, the neural network model may use the a priori knowledge of the target object as a constraint condition, and map the weakly supervised annotation information and the medical image data, to obtain the pseudo segmentation mask. In another example, the neural network model may alternatively use the a priori knowledge of the target object and the weakly supervised annotation information as a constraint condition, and map the medical image data, to obtain the pseudo segmentation mask. In still another example, the medical image data may be mapped based on the a priori knowledge in combination with the unsupervised learning model, to implement image segmentation, so as to obtain an initial pseudo segmentation mask, and the initial pseudo segmentation mask and the weakly supervised annotation are then combined, to determine the pseudo segmentation mask for the target object in the medical image data.

Based on the medical image segmentation method in this embodiment, when the pseudo segmentation mask for the target object in the medical image data is determined, the a priori knowledge of the target object and the weakly supervised annotation information are combined. In this way, the increase of guidance of the a priori knowledge can avoid generating some obvious errors, so as to improve the accuracy of the pseudo segmentation mask obtained through mapping, thereby improving the accuracy of the medical image segmentation.

In an embodiment, the weakly supervised annotation information includes bounding box information, apostrophe annotation information, or point annotation information.

The bounding box annotation information is information of a bounding box that performs annotation for the target object. The bounding box annotation means that the target object is identified by drawing a bounding box on an image. The apostrophe annotation information is information of an apostrophe annotation that performs annotation for the target object. The apostrophe annotation means that the segmented object is identified by drawing an apostrophe on an image. The point annotation information is information of a point annotation that performs annotation for the target object. The point annotation means that the target object is identified by drawing a point on an image. That is, that the target object is at the position annotated by this point can be represented in at least one point annotation manner; or that the target object is at the position annotated by this apostrophe can be represented in at least one apostrophe annotation manner; or that the target object is within a range annotated by this bounding box can be represented in at least one bounding box annotation manner. In this way, labor costs of manual annotation can be reduced, thereby reducing the labor costs of the medical image segmentation.

In an embodiment, the weakly supervised annotation information is the bounding box information. The quality of the segmentation is continuously improved through iterative optimization by using the bounding box annotation as the weakly supervised annotation. In the iterative optimization, all pseudo segmentation masks are used as inputs of next network learning.

In an embodiment, the weakly supervised annotation information is the apostrophe annotation information. An iterative optimization framework is constructed by using a probabilistic graphical model by using the apostrophe annotation as the weakly supervised annotation. Under guidance of the probabilistic graphical model, the apostrophe annotation information is gradually diffused into an unannotated region, so as to obtain complete annotation.

In an embodiment, the foregoing method is implemented by using a neural network model based on medical image segmentation. The inputs of the neural network model based on medical image segmentation are the obtained medical image data and weakly supervised annotation information, and outputs are target segmentation results for the target object. The obtained medical image data and weakly supervised annotation information are inputted to the neural network models based on medical image segmentation, to obtain a target segmentation result for the target object. Because the neural network models based on medical image segmentation segment the medical image data based on the weakly supervised annotation information, there is no need to annotate information by using much labor during training of the neural network models based on medical image segmentation are trained, thereby saving labor costs.

In an embodiment, a training process of the neural network model based on medical image segmentation may include: obtaining a target training object, and obtaining a training sample based on the target training object, the training samples including medical image training data and weakly supervised annotation training information; determining a pseudo segmentation training mask for the target training object in the medical image training data based on the a priori knowledge and the weakly supervised annotation information; and obtaining the neural network models through training based on the pseudo segmentation training mask and the medical image training data.

A person skilled in the art may understand that, the target training object corresponds to the target object, and data structures of the target training object and the target object are the same. The medical image training data corresponds to the medical image data, and data structures of the medical image training data and the medical image data are the same. The weakly supervised annotation training information corresponds to the weakly supervised annotation information, and data structures of the weakly supervised annotation training information and the weakly supervised annotation information are the same. The pseudo segmentation training mask corresponds to the pseudo segmentation mask, and data structures of the pseudo segmentation training mask and the pseudo segmentation mask are the same.

The training samples may use a disclosed Liver Tumor Segmentation Challenge (LiTS) dataset and Atrial Segmentation Challenge (ASC) dataset. For example, bounding box information of a liver region of the LiTS dataset and a left atrium region of the ASC dataset may be extracted as the weakly supervised annotation information, and the unsupervised algorithm such as the Grabcut or the MCG is combined, to generate the pseudo segmentation mask.

It is assumed that $D=\{x_i,s_i\}_{i=1}^{n}$ is n pairs of training samples, and i is a positive integer not greater than n. $x_i \in \mathbb{R}^{h \times w \times c}$ is medical image data of a medical image picture, $s_i \in \mathbb{R}^{h \times w \times c}$ is weakly supervised annotation information corresponding to the medical image data, and h, w, and c are respectively dimensions of the medical image in the coronal, sagittal and axial directions. A pseudo segmentation training mask $y_i \in \mathbb{R}^{h \times w \times c}$ for the target training object in the medical image training data may be determined based on the a priori knowledge and the weakly supervised annotation information. The medical image data may be mapped by using the preset mapping model, to obtain the target segmentation result for the target object. A task of the neural network models is to optimize the loss function. This may be represented as:

$$\min_{\bar{w}} \sum_{i=1}^{n} L(f(\bar{w}; x_i), y_i).$$

f represents the preset mapping model, L represents the loss function, and is used for punishing inconsistency between the prediction result and the real label, and $\bar{w}$ is a parameter of the preset mapping model.

In an embodiment, the obtaining the neural network models through training based on the pseudo segmentation training mask and the medical image training data includes: obtaining a preset mapping model of the neural network model based on medical image segmentation through training based on the pseudo segmentation training mask; inputting the medical image training data to the preset mapping models, to obtain predicted training segmentation results; generating an advanced pseudo segmentation training mask according to the predicted training segmentation results that meet a confidence condition in combination with a priori knowledge; and retraining the preset mapping model according to the advanced pseudo segmentation training mask, until a preset stop condition is met.

The server may use the pseudo segmentation mask obtained in the training process, that is, the pseudo segmentation training mask, as the input of the model, to train the preset mapping models; or may use both the pseudo segmentation mask and the medical image data obtained in the training process, that is, the pseudo segmentation training mask and the medical image training data, as inputs of the preset mapping models, to train the preset mapping models; or may use the pseudo segmentation training mask as a label of the medical image training data in the training process, and perform training based on the label, that is, the pseudo segmentation training mask, and a loss function of the target segmentation results in training, to obtain preset mapping models.

The confidence condition may be that the confidence level is higher than the preset value. The present stop condition may be that a maximum quantity of times of iterations is reached. The maximum quantity of times of iterations may be a set value of a quantity of times of iterations, or may be a quantity of times corresponding to a set iteration time. When the preset stop condition is met, a final preset prediction model is obtained.

Based on the medical image segmentation method in this embodiment, the predicted training segmentation results are screened based on the confidence of the prediction result to obtain an advanced pseudo segmentation mask, so as to screen the training samples, and a next round of model training is performed until the preset stop condition is met, to obtain the preset mapping models. In this way, the training of the neural network model is implemented in a self-paced learning manner, and the selection of confidences of the samples is enhanced, so that the training of the preset mapping models is more stable, thereby improving the stability of the medical image segmentation.

In an embodiment, the training of the at least two preset mapping models is fused into a self-paced learning framework to obtain the neural network model based on medical image segmentation. The formula may be expressed as:

$$E(\bar{w}^j, v_i^j, y_i; \lambda_i^j, \gamma^{j1,j2}, \psi) =$$

$$\sum_{j=1}^{m}\sum_{i=1}^{n} v_i^j L^j(f^j(\bar{w}^j, x_i), y_i) - \sum_{j=1}^{m}\sum_{i=1}^{n} \lambda_i^j v_i^j - \sum_{j1=1}^{m}\sum_{j2=1}^{m} \gamma^{j1,j2}(v_i^{j1})^T v_i^{j2},$$

$$\text{s.t. } v_i^j \in \{0, 1\} \& v_i^j \in \psi_v,$$

$$y_i \in \psi_y$$

i=1, 2, . . . , n represents n pieces of medical image training data, j=1, 2, . . . , m represents m preset mapping models, $f^j$ is a $j^{th}$ preset mapping model, and $\bar{w}^j$ is a parameter of the preset mapping model. $L^j$ is a loss function of the $j^{th}$ preset mapping model, $v_i^j$ indicates whether an $i^{th}$ sample is used for training the $j^{th}$ preset mapping model, and $\gamma$ is a regular term of multi-model fusion. $(v^{j1})^T v^{j2}$ enables that different segmentation networks have the same knowledge of the segmented object. Therefore, prediction results of different segmentation networks are also consistent, so that loss values are also consistent. $\lambda$ is a regular factor of the self-paced learning. $\psi$ represents the a priori knowledge.

Figure 4:
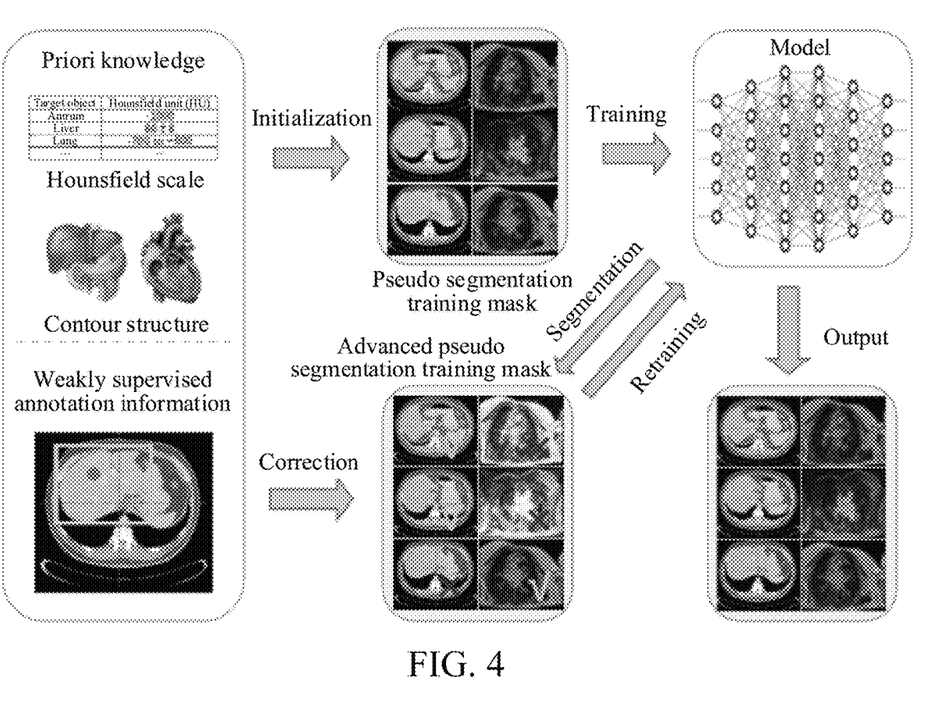
FIG. 4 is a schematic principle diagram of a medical image segmentation method in another exemplary embodiment.

In this embodiment, with reference to FIG. 4, a training process of the neural network model based on medical image segmentation may include:

(1) initialization: In the initialization process, a pseudo segmentation training mask for the target training object in the medical image training data is determined based on the a priori knowledge and the weakly supervised annotation information. In the initialization process, $v^j$ may be initialized. j=1, 2, . . . , m is a vector whose all elements are 1, and it represents that each initialized sample is used for training each preset mapping model. $\lambda^j$ and j=1, 2, . . . , m are fixed vectors. $\gamma$ is a fixed value. In the initialization process, a pseudo segmentation mask may be generated based on the weakly supervised annotation information, the a priori knowledge and an unsupervised learning algorithm.

(2) Training: In the training process, at least two preset mapping models are obtained through training based on the pseudo segmentation training mask.

In the training process, $v^k$, $k \in (1,m)$ & $k \neq j$ is updated for preset mapping models other than the $j^{th}$ preset mapping model. When a sample weight of a current preset mapping model is updated, a physical meaning is that condition predictions of other preset mapping models are considered.

The following formula is obtained by deriving $v^k$ in a framework in which the training of the at least two preset mapping models is fused into the self-paced learning:

$$\frac{\partial E}{\partial v_i^k} = L^k - \lambda_i^k - \sum_{j \neq k}^{m} r^{k,j} v_i^j$$

Further, an updated formula is obtained and may be expressed as:

$$v_i^k = \begin{cases} 1, & \mathcal{L}^k < \lambda_i^k + \sum_{j \neq k}^{m} \Upsilon^{k,j} v_i^j \\ 0, & \text{others} \end{cases},$$

In the training process, $v^j$ needs to be updated for the $j^{th}$ preset mapping model. A training sample is selected for the current preset mapping model according to the prediction condition of the current preset mapping model. In the update process, some unreliable training samples may be screened based on the a priori knowledge $v_i^j \in \psi_v$ of the medical image data.

(3) Segmentation: In the segmentation process, the medical image training data is inputted to the preset mapping models, to obtain predicted training segmentation results. In the segmentation process, $\overline{w}^j$ is updated. The at least two preset mapping models are trained based on the selected training samples.

(4) Correction: An advanced pseudo segmentation training mask is generated according to the predicted training segmentation results that meet a confidence condition in combination with a priori knowledge. That is, $y_i$ is updated. The following formula may be optimized by updating $y_i$:

$$\mathop{\text{argmin}}_{y_i} = \sum_{j=1}^{m} \sum_{i=1}^{n} v_i^j L^j \left( f^j(\overline{w}^j; x_i), y_i \right)$$

$y_i$ may be further corrected in combination with the a priori knowledge $y_i \in \psi_y$ based on the segmentation results.

(5) Retraining: In the retraining process, the preset mapping model is retrained according to the advanced pseudo segmentation training mask, until the preset stop condition is met. That is, the advanced pseudo segmentation training mask is used as a new pseudo segmentation training mask to iteratively perform the steps (2), (3), and (4), until the preset stop condition is met.

When the preset stop condition is met, each preset mapping model is trained, so that the neural network models based on medical image segmentation may be determined. When the medical image data are actually needed to be segmented, the obtained medical image data and weakly supervised annotation information may be inputted to the neural network models based on medical image segmentation, to obtain a segmentation result for the target object.

Steps in the flowchart in FIG. 2 are displayed sequentially based on indication of arrows, but the steps are not necessarily performed sequentially based on the sequence indicated by the arrows. Unless clearly specified in this specification, there is no strict sequence limitation on the execution of the steps, and the steps may be performed in another sequence. In addition, at least some steps in FIG. 2 may include a plurality of substeps or a plurality of stages. The substeps or the stages are not necessarily performed at the same moment, but may be performed at different moments. The substeps or the stages are not necessarily performed in sequence, but may be performed in turn or alternately with another step or at least some of substeps or stages of the other step.

Figure 5:
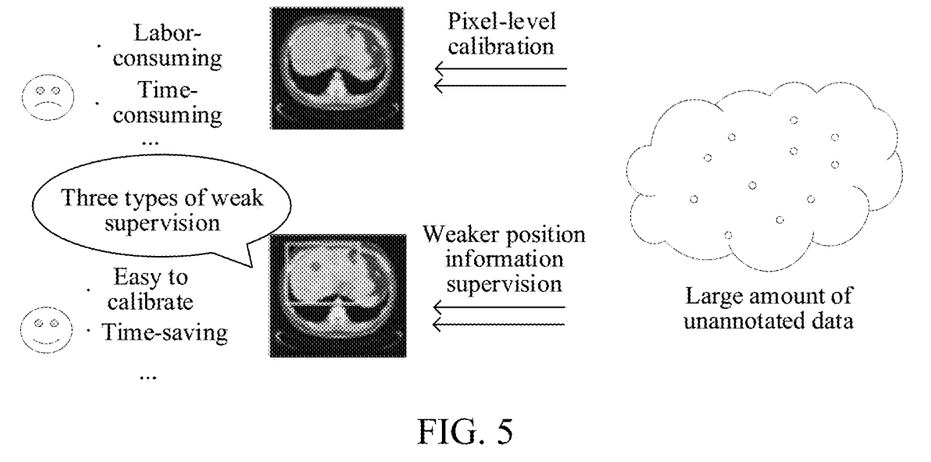
FIG. 5 is a diagram of comparison between a medical image segmentation method and the related technology in an exemplary embodiment.

With reference to FIG. 5, it can be learned that the pixel-level annotation provided in the related technology is labor-consuming and time-consuming. Compared with the related technology, the doctor needs to supervise only a large amount of unannotated data by using weaker position information. That is, in this application, the server may train a better model in a manner of annotating by three types of weak supervision of the annotation information (a point, an apostrophe, or a bounding box). The annotation information of the three types of weak supervision is not only easy to calibrate by the doctor but also very time-saving and labor-saving.

Figure 6:
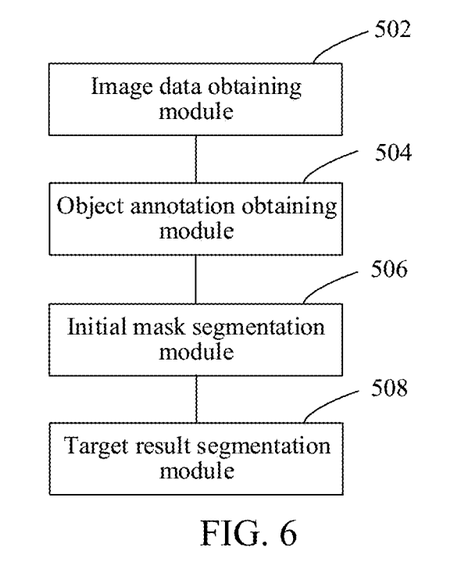
FIG. 6 is a structural block diagram of a medical image segmentation apparatus according to an embodiment.

In an embodiment, as shown in FIG. 6, a medical image segmentation apparatus corresponding to the foregoing medical image segmentation method is provided, including:

a medical image segmentation apparatus, including:
an image data obtaining module 502, configured to obtain medical image data;
an object annotation obtaining module 504, configured to obtain a target object and weakly supervised annotation information of the target object in the medical image data;
an initial mask segmentation module 506, configured to determine a pseudo segmentation mask for the target object in the medical image data according to the weakly supervised annotation information; and
a target result segmentation module 506, configured to perform mapping on the medical image data by using a preset mapping model based on the pseudo segmentation mask, to obtain a target segmentation result for the target object.

In the foregoing medical image segmentation apparatus, medical image data is obtained; a target object and weakly supervised annotation information of the target object in the medical image data are obtained; a pseudo segmentation mask for the target object in the medical image data is determined according to the weakly supervised annotation information; and mapping is performed on the medical image data by using a preset mapping model based on the pseudo segmentation mask, to obtain a target segmentation result for the target object. Because the medical image data is segmented based on the weakly supervised annotation information, there is no need to annotate information by using much labor during training of the preset mapping model used when mapping is performed based on the pseudo segmentation mask and the medical image data, thereby saving labor costs.

In an embodiment, the target result segmentation module includes:
a separate mapping unit, configured to perform mapping on the medical image data based on the pseudo segmentation mask by using at least two preset mapping models, to obtain at least two intermediate segmentation results for the target object; and a result fusion unit, configured to fuse the at least two intermediate segmentation results, to obtain the target segmentation result for the target object.

In an embodiment, the separate mapping unit is further configured to perform mapping on the medical image data based on the pseudo segmentation mask by using at least two neural network models with no less than two structural types, to obtain the at least two intermediate segmentation results for the target object.

In an embodiment, a preset model training module is further included, configured to train the at least two preset mapping models in a self-paced learning manner in a training process of the at least two preset mapping models.

In an embodiment, the preset model training module includes:

an intermediate model training unit, configured to train at least two intermediate preset mapping models based on the pseudo segmentation mask in the training process;

an intermediate result prediction unit, configured to perform mapping on the medical image data in the training process by using the at least two intermediate preset mapping models, to obtain at least two predicted training segmentation results;

an advanced mask generation unit, configured to generate an advanced pseudo segmentation mask according to the predicted training segmentation results that meet a confidence condition in combination with a priori knowledge; and a model iterative training unit, configured to retrain the at least two intermediate preset mapping models based on the advanced pseudo segmentation mask until a preset stop condition is met, to obtain the preset mapping models.

In an embodiment, the target result segmentation module is configured to map the medical image data by using the preset mapping model obtained based on the pseudo segmentation mask, to obtain the target segmentation result for the target object.

In an embodiment, the target result segmentation module includes:

a segmentation result prediction unit, configured to perform mapping based on the pseudo segmentation mask and the medical image data, to obtain a predicted segmentation result for the target object; and a result correction unit, configured to correct the predicted segmentation result according to the a priori knowledge and/or the weakly supervised annotation information, to obtain the target segmentation result.

In an embodiment, the initial mask segmentation module is configured to determine the pseudo segmentation mask for the target object in the medical image data based on the a priori knowledge and the weakly supervised annotation information.

In an embodiment, the weakly supervised annotation information includes bounding box information, apostrophe annotation information, or point annotation information.

In an embodiment, the apparatus is implemented by using a neural network model based on medical image segmentation. That is, the apparatus includes an image data obtaining module, an object annotation obtaining module, an initial mask segmentation module, and a target result segmentation module.

In an embodiment, a neural network training module is further included, the neural network training module being configured to: obtain a target training object, and obtain a training sample based on the target training object, the training samples including medical image training data and weakly supervised annotation training information; determine a pseudo segmentation training mask for the target training object in the medical image training data based on the a priori knowledge and the weakly supervised annotation information; and obtain the neural network models through training based on the pseudo segmentation training mask and the medical image training data.

In an embodiment, the neural network training module is further configured to: obtain a preset mapping model of the neural network model through training based on the pseudo segmentation training mask; input the medical image training data to the preset mapping models, to obtain predicted training segmentation results; generate an advanced pseudo segmentation training mask according to the predicted training segmentation results that meet a confidence condition in combination with a priori knowledge; and retrain the preset mapping model according to the advanced pseudo segmentation training mask, until a preset stop condition is met.

Figure 7:
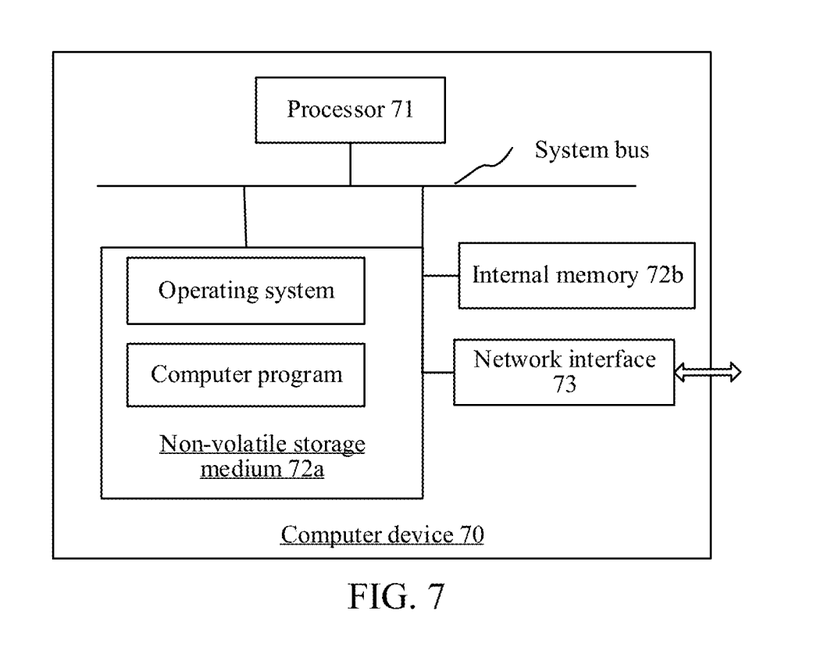
FIG. 7 is a schematic structural diagram of a computer device according to an embodiment.

As shown in FIG. 7, in an embodiment, a computer device 70 is provided. The computer device 70 may be a server or a terminal. The computer device 70 includes a processor 71, a memory 72b, and a network interface 73 that are connected by using a system bus. The processor 71 of the computer device is configured to provide computing and control capabilities. The memory of the computer device includes a non-volatile storage medium 72a and an internal memory 72b. The non-volatile storage medium 72a stores an operating system and a computer program. The internal memory 72b provides an environment for running of the operating system and the computer program in the non-volatile storage medium. The network interface 73 of the computer device is configured to communicate with an external terminal through a network connection. The computer program is executed by the processor to implement a medical image segmentation method. Optionally, the computer device 70 further includes a display screen (not shown) and an input apparatus (not shown).

A person skilled in the art may understand that, the structure shown in FIG. 7 is only a block diagram of a part of a structure related to a solution of this application and does not limit the computer device to which the solution of this application is applied. Specifically, the computer device may include more or fewer components than those in the drawings, or include a combination of some components, or include different component layouts.

In an implementation, a computer device is provided. The computer device may be a server or a terminal. The computer device includes a memory and a processor, the memory storing a computer program, the processor, when executing the computer program, implementing the operations of the foregoing medical image segmentation method.

In an embodiment, the computer device includes a memory and a processor, the memory storing a computer program, the processor, when executing the computer program, implementing the following operations:

obtaining medical image data;

obtaining a target object and weakly supervised annotation information of the target object in the medical image data;

determining a pseudo segmentation mask for the target object in the medical image data according to the weakly supervised annotation information; and performing mapping on the medical image data by using a preset mapping model based on the pseudo segmentation mask, to obtain a target segmentation result for the target object.

In an embodiment, the performing mapping on the medical image data by using a preset mapping model based on the pseudo segmentation mask, to obtain a target segmentation result for the target object includes:
  performing mapping on the medical image data based on the pseudo segmentation mask by using at least two preset mapping models, to obtain at least two intermediate segmentation results for the target object; and
  fusing the at least two intermediate segmentation results, to obtain the target segmentation result for the target object.

In an embodiment, the performing mapping on the medical image data based on the pseudo segmentation mask by using at least two preset mapping models, to obtain at least two intermediate segmentation results for the target object includes:
  performing mapping on the medical image data based on the pseudo segmentation mask by using at least two neural network models with no less than two structural types, to obtain the at least two intermediate segmentation results for the target object.

In an embodiment, in a training process of the at least two preset mapping models, the at least two preset mapping models are trained in a self-paced learning manner.

In an embodiment, the training process of the at least two preset mapping models includes:
  training at least two intermediate preset mapping models based on the pseudo segmentation mask in the training process;
  performing mapping on the medical image data in the training process by using the at least two intermediate preset mapping models, to obtain at least two predicted training segmentation results;
  generating an advanced pseudo segmentation mask according to the predicted training segmentation results that meet a confidence condition in combination with a priori knowledge; and
  retraining the at least two intermediate preset mapping models based on the advanced pseudo segmentation mask until a preset stop condition is met, to obtain the preset mapping models.

In an embodiment, the mapping, based on the pseudo segmentation mask, of the medical image data by using a preset mapping model, to obtain a target segmentation result for the target object includes:
  mapping the medical image data by using the preset mapping model obtained based on the pseudo segmentation mask, to obtain the target segmentation result for the target object.

In an embodiment, the mapping of the medical image data based on the pseudo segmentation mask, to obtain a target segmentation result for the target object includes:
  performing mapping on the medical image data based on the pseudo segmentation mask, to obtain a predicted segmentation result for the target object; and
  correcting the predicted segmentation result according to the a priori knowledge and/or the weakly supervised annotation information, to obtain the target segmentation result.

In an embodiment, the determining a pseudo segmentation mask for the target object in the medical image data according to the weakly supervised annotation information includes:
  determining the pseudo segmentation mask for the target object in the medical image data based on the a priori knowledge and the weakly supervised annotation information.

In an embodiment, the weakly supervised annotation information includes bounding box information, apostrophe annotation information, or point annotation information.

In an embodiment, the computer program is implemented by using a neural network model based on medical image segmentation.

In an embodiment, a training process of the neural network model based on medical image segmentation includes:
  obtaining a target training object, and obtaining a training sample based on the target training object, the training samples including medical image training data and weakly supervised annotation training information;
  determining a pseudo segmentation training mask for the target training object in the medical image training data based on the a priori knowledge and the weakly supervised annotation information; and
  obtaining the neural network models through training based on the pseudo segmentation training mask and the medical image training data.

In an embodiment, the obtaining the neural network models through training based on the pseudo segmentation training mask and the medical image training data includes:
  obtaining a preset mapping model of the neural network model through training based on the pseudo segmentation training mask;
  inputting the medical image training data to the preset mapping models, to obtain predicted training segmentation results;
  generating an advanced pseudo segmentation training mask according to the predicted training segmentation results that meet a confidence condition in combination with a priori knowledge; and
  retraining the preset mapping model according to the advanced pseudo segmentation training mask, until a preset stop condition is met.

In an embodiment, a computer-readable storage medium is provided, storing a computer program, the computer program, when executed by a processor, implementing the operations of the foregoing medical image segmentation method.

In an embodiment, a computer-readable storage medium is provided, storing a computer program, the computer program, when executed by a processor, implementing the following operations:
  obtaining medical image data;
  obtaining a target object and weakly supervised annotation information of the target object in the medical image data;
  determining a pseudo segmentation mask for the target object in the medical image data according to the weakly supervised annotation information; and
  performing mapping on the medical image data based on the pseudo segmentation mask by using a preset mapping model, to obtain a target segmentation result for the target object.

In an embodiment, the mapping of the medical image data based on the pseudo segmentation mask by using a preset mapping model, to obtain a target segmentation result for the target object includes:
  performing mapping on the medical image data based on the pseudo segmentation mask by using at least two preset mapping models, to obtain at least two intermediate segmentation results for the target object; and fusing the at least two intermediate segmentation results, to obtain the target segmentation result for the target object.

In an embodiment, the mapping of the medical image data based on the pseudo segmentation mask by using at least two preset mapping models, to obtain at least two intermediate segmentation results for the target object includes:

performing mapping on the medical image data based on the pseudo segmentation mask by using at least two neural network models with no less than two structural types, to obtain the at least two intermediate segmentation results for the target object.

In an embodiment, in a training process of the at least two preset mapping models, the at least two preset mapping models are trained in a self-paced learning manner.

In an embodiment, the training process of the at least two preset mapping models includes:

training at least two intermediate preset mapping models based on the pseudo segmentation mask in the training process;

performing mapping on the medical image data in the training process by using the at least two intermediate preset mapping models, to obtain at least two predicted training segmentation results;

generating an advanced pseudo segmentation mask according to the predicted training segmentation results that meet a confidence condition in combination with a priori knowledge; and retraining the at least two intermediate preset mapping models based on the advanced pseudo segmentation mask until a preset stop condition is met, to obtain the preset mapping models.

In an embodiment, the mapping of the medical image data based on the pseudo segmentation mask by using a preset mapping model, to obtain a target segmentation result for the target object includes:

mapping the medical image data by using the preset mapping model obtained based on the pseudo segmentation mask, to obtain the target segmentation result for the target object.

In an embodiment, the mapping of the medical image data based on the pseudo segmentation mask, to obtain a target segmentation result for the target object includes:

performing mapping on the medical image data based on the pseudo segmentation mask, to obtain a predicted segmentation result for the target object; and correcting the predicted segmentation result according to the a priori knowledge and/or the weakly supervised annotation information, to obtain the target segmentation result.

In an embodiment, the determining a pseudo segmentation mask for the target object in the medical image data according to the weakly supervised annotation information includes:

determining the pseudo segmentation mask for the target object in the medical image data based on the a priori knowledge and the weakly supervised annotation information.

In an embodiment, the weakly supervised annotation information includes bounding box information, apostrophe annotation information, or point annotation information.

In an embodiment, the computer program is implemented by using a neural network model based on medical image segmentation.

In an embodiment, a training process of the neural network model based on medical image segmentation includes:

obtaining a target training object, and obtaining a training sample based on the target training object, the training samples including medical image training data and weakly supervised annotation training information;

determining a pseudo segmentation training mask for the target training object in the medical image training data based on the a priori knowledge and the weakly supervised annotation information; and obtaining the neural network models through training based on the pseudo segmentation training mask and the medical image training data.

In an embodiment, the obtaining the neural network models through training based on the pseudo segmentation training mask and the medical image training data includes:

obtaining a preset mapping model of the neural network model through training based on the pseudo segmentation training mask;

inputting the medical image training data to the preset mapping models, to obtain predicted training segmentation results;

generating an advanced pseudo segmentation training mask according to the predicted training segmentation results that meet a confidence condition in combination with a priori knowledge; and retraining the preset mapping model according to the advanced pseudo segmentation training mask, until a preset stop condition is met.

Figure 8:
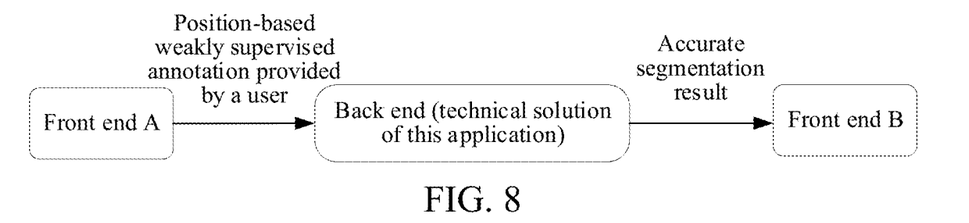
FIG. 8 is a schematic diagram of implementing a medical image segmentation method using a cloud computing architecture in an embodiment.

In examples shown in FIG. 8, the foregoing neural network model is disposed in a back end. The back end is a server end built using a cloud computing architecture. A front end A receives a medical image and a position information annotation that are inputted by a user. The position information annotation is a position-based weakly supervised annotation. The back end maps the medical image according to the position information annotation, to obtain an accurate segmentation result of a target organ in the medical image, and transmits the accurate segmentation result to a front end B device. The front end A may be a device used by a user, and the front end B may be a device used by a doctor.

A person of ordinary skill in the art may understand that some or all procedures in the foregoing method embodiments may be implemented by a computer program instructing related hardware. The computer program may be stored in a non-volatile computer-readable storage medium, and when the computer program is executed, the procedures of the foregoing method embodiments may be performed. Any reference to a memory, a storage, a database, or another medium used in the embodiments provided in this application may include a non-volatile and/or volatile memory. The non-volatile memory may include a read-only memory (ROM), a programmable ROM (PROM), an electrically programmable ROM (EPROM), an electrically erasable programmable ROM (EEPROM), a flash memory, or the like. The volatile memory may include a random access memory (RAM) or an external cache. As an illustration instead of a limitation, the RAM is available in various forms, such as a static RAM (SRAM), a dynamic RAM (DRAM), a synchronous DRAM (SDRAM), a double data rate SDRAM (DDRSDRAM), an enhanced SDRAM (ESDRAM), a synchronization link (Synchlink) DRAM (SLDRAM), a Rambus direct RAM (RDRAM), a direct Rambus dynamic RAM (DRDRAM), and a Rambus dynamic RAM (RDRAM).

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

The foregoing embodiments only describe several implementations of this application, which are described specifically and in detail, but cannot be construed as a limitation to the patent scope of this application. For a person of ordinary skill in the art, several transformations and improvements can be made without departing from the idea of this application. These transformations and improvements belong to the protection scope of this application. Therefore, the protection scope of the patent of this application shall be subject to the appended claims.

What is claimed is:

1. A medical image segmentation method, applicable to a computer device, the method comprising:
    obtaining medical image data;
    obtaining a target object and weakly supervised annotation information of the target object in the medical image data;
    determining a pseudo segmentation mask for the target object in the medical image data according to the weakly supervised annotation information; and
    performing mapping on the medical image data by using a preset mapping model based on the pseudo segmentation mask, to obtain a target segmentation result for the target object, further comprising:
        performing mapping on the medical image data based on the pseudo segmentation mask by using at least two preset mapping models, to obtain at least two intermediate segmentation results for the target object; and
        fusing the at least two intermediate segmentation results, to obtain the target segmentation result for the target object.

2. The method according to claim 1, wherein the performing mapping on the medical image data based on the pseudo segmentation mask by using at least two preset mapping models, to obtain at least two intermediate segmentation results for the target object comprises:
    performing mapping on the medical image data based on the pseudo segmentation mask and by using at least two neural network models with no less than two structural types, to obtain the at least two intermediate segmentation results for the target object.

3. The method according to claim 1, wherein in a training process of the at least two preset mapping models, the at least two preset mapping models are trained in a self-paced learning manner.

4. The method according to claim 3, wherein the training process of the at least two preset mapping models comprises:
    training at least two intermediate preset mapping models based on the pseudo segmentation mask in the training process;
    performing mapping on the medical image data in the training process by using the at least two intermediate preset mapping models, to obtain at least two predicted training segmentation results;
    generating an advanced pseudo segmentation mask according to the predicted training segmentation results in the at least two predicted training segmentation results that meet a confidence condition in combination with a priori knowledge; and
    retraining the at least two intermediate preset mapping models based on the advanced pseudo segmentation mask until a preset stop condition is met, to obtain the preset mapping models.

5. The method according to claim 1, wherein the performing mapping on the medical image data by using a preset mapping model based on the pseudo segmentation mask, to obtain a target segmentation result for the target object comprises:
    mapping the medical image data by using the preset mapping model obtained based on the pseudo segmentation mask, to obtain the target segmentation result for the target object.

6. The method according to claim 1, wherein the performing mapping on the medical image data by using a preset mapping model based on the pseudo segmentation mask, to obtain a target segmentation result for the target object comprises:
    performing mapping on the medical image data based on the pseudo segmentation mask to obtain a predicted segmentation result for the target object; and
    correcting the predicted segmentation result according to the a priori knowledge and/or the weakly supervised annotation information, to obtain the target segmentation result of the target object.

7. The method according to claim 1, wherein the determining a pseudo segmentation mask for the target object in the medical image data according to the weakly supervised annotation information comprises:
    determining the pseudo segmentation mask for the target object in the medical image data based on the a priori knowledge and the weakly supervised annotation information.

8. The method according to claim 1, wherein the weakly supervised annotation information comprises bounding box information, apostrophe annotation information, or point annotation information.

9. The method according to claim 1, wherein the method is implemented by using a neural network model based on medical image segmentation.

10. The method according to claim 9, wherein a training process of the neural network model based on medical image segmentation comprises:
    obtaining a target training object, and obtaining training samples based on the target training object, the training samples comprising medical image training data and weakly supervised annotation training information;
    determining a pseudo segmentation training mask for the target training object in the medical image training data based on the a priori knowledge and the weakly supervised annotation information; and
    obtaining the neural network models through training based on the pseudo segmentation training mask and the medical image training data.

11. The method according to claim 10, wherein the obtaining the neural network models through training based on the pseudo segmentation training mask and the medical image training data comprises:
    obtaining a preset mapping model of the neural network model through training based on the pseudo segmentation training mask;
    inputting the medical image training data to the preset mapping models, to obtain predicted training segmentation results;
    generating an advanced pseudo segmentation training mask according to the predicted training segmentation results that meet a confidence condition in combination with a priori knowledge; and retraining the preset mapping model according to the advanced pseudo segmentation training mask, until a preset stop condition is met.

12. A computer device, comprising a memory and a processor, the memory storing a plurality of computer programs that, when executed by the processor, cause the computer device to perform a plurality of operations including:

obtaining medical image data;

obtaining a target object and weakly supervised annotation information of the target object in the medical image data;

determining a pseudo segmentation mask for the target object in the medical image data according to the weakly supervised annotation information; and performing mapping on the medical image data by using a preset mapping model based on the pseudo segmentation mask, to obtain a target segmentation result for the target object, further comprising:

performing mapping on the medical image data based on the pseudo segmentation mask by using at least two preset mapping models, to obtain at least two intermediate segmentation results for the target object; and fusing the at least two intermediate segmentation results, to obtain the target segmentation result for the target object.

13. The computer device according to claim 12, wherein the performing mapping on the medical image data based on the pseudo segmentation mask by using at least two preset mapping models, to obtain at least two intermediate segmentation results for the target object comprises:

performing mapping on the medical image data based on the pseudo segmentation mask and by using at least two neural network models with no less than two structural types, to obtain the at least two intermediate segmentation results for the target object.

14. The computer device according to claim 12, wherein the performing mapping on the medical image data by using a preset mapping model based on the pseudo segmentation mask, to obtain a target segmentation result for the target object comprises:

mapping the medical image data by using the preset mapping model obtained based on the pseudo segmentation mask, to obtain the target segmentation result for the target object.

15. The computer device according to claim 12, wherein the performing mapping on the medical image data by using a preset mapping model based on the pseudo segmentation mask, to obtain a target segmentation result for the target object comprises:

performing mapping on the medical image data based on the pseudo segmentation mask to obtain a predicted segmentation result for the target object; and correcting the predicted segmentation result according to the a priori knowledge and/or the weakly supervised annotation information, to obtain the target segmentation result of the target object.

16. The computer device according to claim 12, wherein the determining a pseudo segmentation mask for the target object in the medical image data according to the weakly supervised annotation information comprises:

determining the pseudo segmentation mask for the target object in the medical image data based on the a priori knowledge and the weakly supervised annotation information.

17. The computer device according to claim 12, wherein the weakly supervised annotation information comprises bounding box information, apostrophe annotation information, or point annotation information.

18. A non-transitory computer-readable storage medium, storing a plurality of computer programs that, when executed by a processor of a computer device, cause the computer device to perform a plurality of operations including:

obtaining medical image data;

obtaining a target object and weakly supervised annotation information of the target object in the medical image data;

determining a pseudo segmentation mask for the target object in the medical image data according to the weakly supervised annotation information; and performing mapping on the medical image data by using a preset mapping model based on the pseudo segmentation mask, to obtain a target segmentation result for the target object;

performing mapping on the medical image data by using a preset mapping model based on the pseudo segmentation mask, to obtain a target segmentation result for the target object, further comprising:

performing mapping on the medical image data based on the pseudo segmentation mask by using at least two preset mapping models, to obtain at least two intermediate segmentation results for the target object; and fusing the at least two intermediate segmentation results, to obtain the target segmentation result for the target object.

19. The non-transitory computer-readable storage medium according to claim 18, wherein the performing mapping on the medical image data based on the pseudo segmentation mask by using at least two preset mapping models, to obtain at least two intermediate segmentation results for the target object comprises:

performing mapping on the medical image data based on the pseudo segmentation mask and by using at least two neural network models with no less than two structural types, to obtain the at least two intermediate segmentation results for the target object.

20. The non-transitory computer-readable storage medium according to claim 18, wherein the determining a pseudo segmentation mask for the target object in the medical image data according to the weakly supervised annotation information comprises:

determining the pseudo segmentation mask for the target object in the medical image data based on the a priori knowledge and the weakly supervised annotation information.

* * * * *